(12) United States Patent
Douglass, III et al.

(10) Patent No.: US 7,504,497 B2
(45) Date of Patent: *Mar. 17, 2009

(54) ORALLY BIOAVAILABLE COMPOUNDS AND METHODS FOR INHIBITING PLATELET AGGREGATION

(75) Inventors: James G. Douglass, III, Apex, NC (US);
Paul S. Watson, Carrboro, NC (US);
Carl A. Samuelson, Durham, NC (US);
Christopher S. Crean, Pittsboro, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/595,837

(22) Filed: Nov. 9, 2006

(65) Prior Publication Data

US 2007/0093446 A1    Apr. 26, 2007

Related U.S. Application Data

(63) Continuation-in-part of application No. PCT/US2006/017781, filed on May 5, 2006, which is a continuation-in-part of application No. 11/124,619, filed on May 5, 2005, now Pat. No. 7,335,648.

(51) Int. Cl.
C07H 19/16    (2006.01)
A01N 43/04    (2006.01)
A61K 31/70    (2006.01)

(52) U.S. Cl. ............................. 536/27.3; 514/46
(58) Field of Classification Search ............... None
See application file for complete search history.

(56) References Cited

U.S. PATENT DOCUMENTS

| | | | |
|---|---|---|---|
| 5,049,550 A | 9/1991 | Zamecnik | 514/47 |
| 5,681,823 A | 10/1997 | Kim et al. | 514/47 |
| 5,747,496 A | 5/1998 | Cox et al. | 514/258 |
| 6,037,343 A | 3/2000 | Ali | 514/252 |
| 6,040,317 A | 3/2000 | Duggan et al. | 514/317 |
| 6,048,865 A | 4/2000 | Baraldi | |
| 6,297,232 B1 | 10/2001 | Bonnert et al. | 514/211.03 |
| 6,369,064 B1 | 4/2002 | Brown et al. | 514/258 |
| 2002/0052337 A1 | 5/2002 | Boyer et al. | |
| 2005/0159388 A1 | 7/2005 | Plourde et al. | 514/45 |
| 2005/0250729 A1 | 11/2005 | Baraldi et al. | |
| 2005/0267134 A1 | 12/2005 | Plourde et al. | 514/263.22 |
| 2006/0121086 A1 | 6/2006 | Boyer et al. | 424/426 |
| 2007/0123544 A1 | 5/2007 | Plourde et al. | |

FOREIGN PATENT DOCUMENTS

| | | | |
|---|---|---|---|
| WO | WO 98/28300 A1 | 7/1998 |
| WO | WO 99/05142 A1 | 2/1999 |
| WO | WO 99/05143 A1 | 2/1999 |
| WO | WO 99/05144 A1 | 2/1999 |
| WO | WO 99/41254 A1 | 8/1999 |
| WO | WO 00/04021 A1 | 1/2000 |
| WO | WO 01/36438 A1 | 5/2001 |
| WO | WO 02/16381 A2 | 2/2002 |
| WO | WO 02/096428 A1 | 12/2002 |
| WO | WO 2005040174 | 5/2005 |

OTHER PUBLICATIONS

Vippagunta et al. Advanced Drug Delivery Reviews 48 (2001) 3-26.*
Abstracts of Papers, 225TH ACS National Meeting, New Orleans, LA; Mar. 2003; MEDI-016.
André, et al., "P2Y$_{12}$ regulates platelet adhesion/activation, thrombus growth, and thrombus stability in injured arteries," *J. Clin. Invest.*, 112: 398-406 (2003).
Bennett, et al., "Thrombotic Thrombocytopenic Purpura Associated with Ticlopidine," *Ann. Intern. Med.* 128: 541-544 (1998).
Bennett, et al., "Thrombotic Thrombocytopenic Purpura Associated with Clopidogrel," *N. Engl. J. Med.* 342: 1771-1777 (2000).
Bernat, et al., "Effect of Various Antiplatelet Agents on Acute Arterial Thrombosis in the Rat," *Thromb. Haemostas.* 70: 812-826 (1993).
Dangelmaier, et al., "Potentiation of Thromboxane A$_2$-induced Platelet Secretion by Gi Signaling through the Phospholnosltide-3 Kinase Pathway," *Thromb. Haemostas.* 85: 341-348 (2001).
The EPIC investigators; Califf, R.M. coordinating author; "Use of a Monoclonal Antibody Directed Against the Platelet Glycoprotein IIb/IIIa Receptor in High-Risk Coronary Angioplasty," *New Engl. J. Med.* 330: 956-961 (1994).
Gachet, C., "ADP Receptors of Platelets and their Inhibition," *Thromb. Haemostas.* 86: 222-232 (2001).
Geiger, et al., "Specific Impairment of Human Platelet P2Y$_{AC}$ ADP Receptor-Mediated Signaling by the Antiplatelet Drug Clopidogrel," *Arterioscler. Thromb. Vasc. Biol.* 19: 2007-2011 (1999).
Hass, et al., "A Randomized Trial Comparing Ticlopidine Hydrochloride with Aspirin for the Prevention of Stroke in High-Risk Patients," *N. Engl. J. Med.* 321: 501-507 (1989).
Hechler, et al., "A Role of the Fast ATP-gated P2X$_1$ Cation Channel in Thrombosis of Small Arteries In Vivo," *J. Exp. Med.* 198: 661-667 (2003).
Herbert, et al., "Inhibitory Effect of Clopidogrel on Platelet Adhesion and Intimal Proliferation After Arterial Injury in Rabbits," *Arterioscl. Thromb.* 13: 1171-1179 (1993).

(Continued)

Primary Examiner—Shaojia Anna Jiang
Assistant Examiner—Layla Bland
(74) *Attorney, Agent, or Firm*—Howrey LLP; Viola T. Kung

(57) ABSTRACT

This invention is directed to a method of preventing or treating diseases or conditions associated with platelet aggregation. The method is also directed to a method of treating thrombosis or related disorders. The method comprises administering to a subject a pharmaceutical composition comprising an effective amount of a non-nucleotide compound, preferably a P2Y$_{12}$ receptor antagonist compound, wherein said amount is effective to inhibit platelet aggregation. The compounds useful for this invention include compounds of general Formulae III, IIIa, and IIIb, or salts, hydrates, and solvates thereof. The present invention also provides novel compounds of Formulae IIIa and IIIb, which are potent and have a good oral bioavailability.

18 Claims, No Drawings

OTHER PUBLICATIONS

Hourani, et al., "Effects of the $P_2$-purinoceptor antagonist, suramin, on human platelet aggregation induced by adenosine 5'-diphosphate," *Br. J. Pharmacology* 105: 453-457 (1992).

The IMPACT-II investigators; "Randomised placebo-controlled trial of effect of eptifibatide on complications of percutaneous coronary intervention: IMPACT-II," *Lancet* 349: 1422-1428 (1997).

Ingall, et al., "Antagonists of the Platelet $P_{2T}$ Receptor: A Novel Approach to Antithrombotic Therapy," *J. Med. Chem.* 42: 213-220 (1999).

Jagroop, et al., "Both the ADP receptors $P2Y_1$ and $P2Y_{12}$, play a roll in controlling shape change in human platelets," *Platelets* 14: 15-20 (2003).

Kapetanakis, et al., "Clopidogrel administration prior to coronary artery bypass grafting surgery: the cardiologist's panacea or the surgeon's headache?, " *Eur Heat J.* 26:576-83 (2005).

Lekstrom and Bell, "Aspirin in the Prevention of Thrombosis," *Medicine* 70: 161-177 (1991).

Maffrand, et al., "ADP Plays a Key Role in Thrombogenesis in Rats," *Thromb. Haemostas.* 59: 225-230 (1988).

Neuhaus, et al., "Safety Observations from the Pilot Phase of the Radomized r-Hirudin for Improvement of Thrombolysis (HIT-III) Study," *Circulation*, 90: 1638-1642 (1994).

Quinn and Fitzgerald, "Ticlopidine and Clopidogrel," *Circulation* 100: 1667-1672 (1999).

The Restore investigators; "Effects of Platelet Glycoprotein IIb/IIIa Blockade with Tirofiban on Adverse Cardiac Events in Patients with Unstable Angina or Acute Myocardial Infarction Undergoing Coronary Angioplasty," *Circulation* 96: 1445-1453 (1997).

Savi, et al., "Identification and Biological Activity of the Active Metabolite of Clopidogrel," *Thromb. Haemostas.* 84: 891-896 (2000).

Weber, et al., "Low-Dose Aspirin Verus Anticoagulants for Prevention of Coronary Graft Occlusion,"*Am. J. Cardiol* 66: 1461-1468 (1990).

International Search Report for PCT/US06/17781, mailed Jan. 29, 2008.

* cited by examiner

ORALLY BIOAVAILABLE COMPOUNDS AND METHODS FOR INHIBITING PLATELET AGGREGATION

This application is a continuation-in-part of PCT/US2006/017781, filed May 5, 2006; which is a continuation-in-part of U.S. application Ser. No. 11/124,619, filed May 5, 2005 now U.S. Pat. No. 7,335,648. The contents of all the above-identified applications are incorporated herein by reference in their entirety.

TECHNICAL FIELD

This invention relates to non-nucleotide compounds and methods of using such compounds in the prevention or treatment of diseases or conditions associated with platelet aggregation, including thrombosis, stroke and myocardial infarction in humans and other mammals. The compounds are suitable for oral administration.

BACKGROUND OF THE INVENTION

Hemostasis is the spontaneous process of arresting bleeding from damaged blood vessels. Upon injury, precapillary vessels contract within seconds, and thrombocytes, or blood platelets, bind to the exposed subendothelial matrix of an injured vessel by a process called platelet adhesion. Platelets also stick to each other in a phenomenon known as platelet aggregation to form stable platelet aggregates that quickly help stop or slow blood outflow from injured vessels.

An intravascular thrombus can result from pathological disturbances of hemostasis, or by the rupture of atherosclerotic plaques. Platelet adhesion and aggregation are critical events in intravascular thrombosis. Activated under conditions of high shear blood flow in diseased vessels or by the release of mediators from other circulating cells and damaged endothelial cells lining the vessel, platelets and other cells accumulate at a site of vessel injury to form a thrombus, and recruit more platelets to the developing thrombus. The thrombus can grow to sufficient size to block off arterial blood vessels. Thrombi can also form in areas of stasis or slow blood flow in veins. Venous thrombi can easily detach portions of themselves, creating emboli that travel through the circulatory system. This process can result in blockade of other vessels, such as pulmonary arteries. Blockages of this sort can result in pathological outcomes such as pulmonary embolism. Thus, arterial thrombi cause serious disease by local blockade, whereas the morbidity and mortality associated with venous thrombi arise primarily after distant blockade, or embolization. Conditions associated with pathological thrombus formation include venous thromboembolism, thrombophlebitis, deep vein thrombosis, arterial embolism, coronary and cerebral arterial thrombosis, unstable angina, myocardial infarction, stroke, transient ischemic attack, cerebral embolism, renal embolism and pulmonary embolism.

A number of converging pathways lead to platelet aggregation. Whatever the initial stimulus, the final common event is crosslinking of platelets by binding of fibrinogen to a membrane binding site, glycoprotein IIb/IIIa (GP IIb/IIIa, also known as integrin $\alpha_{IIb}\beta_3$). Antagonists of the GP IIb/IIIa receptor have been shown to produce potent antithrombotic effects (Ali, U.S. Pat. No. 6,037,343; Duggan, et al., U.S. Pat. No. 6,040,317). GP IIb/IIIa antagonists include function-blocking antibodies like Abciximab (ReoPro®), cyclic peptides and peptidomimetic compounds (The EPIC investigators; Califf, R. M., coordinating author, New Engl. J. Med. 330: 956-961 (1994); The IMPACT-II investigators, Lancet 349:1422-1428 (1997); The RESTORE investigators, Circulation 96: 1445-1453 (1997)). The clinical efficacy of some of these newer drugs, such as Abciximab, is impressive, but recent trials have found that these approaches are associated with an increased risk of major bleeding, sometimes necessitating blood transfusion (The EPIC investigators; Califf, R. M., coordinating author, New Engl. J Med. 330: 956-961 (1994)). Also, administration of this class of antiplatelet agent appears to be limited to intravenous methods.

Thrombin can produce platelet aggregation independently of other pathways but substantial quantities of thrombin are unlikely to be present without prior activation of platelets by other mechanisms. Thrombin inhibitors, such as hirudin, are highly effective antithrombotic agents. However, functioning as both antiplatelet and anti-coagulant agents, thrombin inhibitors again can produce excessive bleeding (The TIMI 9a Investigators, Circulation, 90: 1624-1630 (1994); The GUSTO IIa Investigators, Circulation, 90: 1631-1637 (1994); Neuhaus, et al., Circulation, 90: 1638-1642 (1994)).

Various antiplatelet agents have been studied as inhibitors of thrombus formation. Some agents such as aspirin and dipyridamole have come into use as prophylactic antithrombotic agents, and others have been the subjects of clinical investigations. To date, therapeutic agents such as the disintegrins, and the thienopyridines ticlopidine (TICLID®) and clopidogrel (PLAVIX®) have been shown to have utility as platelet aggregation inhibitors, although they can produce a substantial number of side effects and have limited effectiveness in some patients. (Hass, et al., N. Engl. J. Med., 321: 501-507 (1989); Weber, et al., Am. J. Cardiol. 66: 1461-1468 (1990); Lekstrom and Bell, Medicine 70: 161-177 (1991)). In particular, the use of the thienopyridines in antiplatelet therapies has been shown to increase the incidence of potentially life threatening thrombotic thrombocytopenic purpura (Bennett, et al., N. Engl. J. Med, 342: 1771-1777 (2000)). Aspirin, which has a beneficial effect on the inhibition of platelet aggregation (Antiplatelet Trialists' Collaboration, Br. Med. J. 308: 81-106 (1994); Antiplatelet Trialists' Collaboration, Br. Med. J. 308: 159-168 (1994)), acts by inhibiting the synthesis of prostaglandins. Its well-documented, high incidence of gastric side effects, however, limits its usefulness in many patients. In addition, aspirin resistance has been observed in some individuals (McKee, et al., Thromb. Haemost. 88: 711-715 (2002)).

Many studies have demonstrated that adenosine 5'-diphosphate (ADP) plays a key role in the initiation and progression of arterial thrombus formation (Bemat, et al., Thromb. Haemostas. 70: 812-826 (1993)); Maffrand, et al., Thromb. Haemostas. 59: 225-230 (1988); Herbert, et al., Arterioscl. Thromb. 13: 1171-1179 (1993)). ADP induces inhibition of adenylyl cyclase and modulation of intracellular signaling pathways such as activation of phosphoinositide-3 kinase (P13K), influx and mobilization of intracellular $Ca^{+2}$, secretion, shape change, and platelet aggregation (Dangelmaier, et al. Thromb Haemost. 85: 341-348 (2001)). ADP-induced platelet aggregation is triggered by its binding to specific receptors expressed in the plasma membrane of the platelet. There are at least three different P2 receptors expressed in human platelets: $P2X_1$, $P2Y_1$, and $P2Y_{12}$. The $P2X_1$ receptor is a ligand-gated cation channel that is activated by ATP, resulting in a transient influx of extracellular calcium. This receptor has been implicated in the regulation of platelet shape change, and recent evidence suggests its participation in thrombus formation in small arteries under high shear forces. (Jagroop, et al., Platelets 14:15-20 (2003); Hechler, et al., J. Exp. Med. 198: 661-667 (2003)). The $P2Y_1$ receptor is a G protein-coupled receptor that is activated by ADP, and is responsible for calcium mobilization from intracellular stores, platelet shape change and initiation of aggregation. The $P2Y_{12}$ receptor, also referred to as the $P2Y_{ac}$ and $P2_T$ receptor, is a G protein-coupled receptor that is activated by ADP and is responsible for inhibition of adenylyl cyclase and activation of P13K. Activation of $P2Y_{12}$ is required for platelet secretion and stabilization of platelet aggregates (Gachet, *Thromb. Haemost.* 86: 222-232 (2001); André, et al., *J. Clin. Invest.,* 112: 398-406 (2003)).

ADP-induced platelet aggregation requires the simultaneous activation of both $P2Y_1$ and $P2Y_{12}$ receptors, and therefore, aggregation can be inhibited by blockade of either receptor. Several authors have demonstrated that ADP-induced aggregation is inhibited in a concentration-dependent manner by analogues of adenosine triphosphate (ATP). ATP, itself, is a weak and nonselective, but competitive, $P2Y_1$ and $P2Y_{12}$ receptor antagonist. Ingall, et al. (*J. Med. Chem.* 42: 213-220 (1999)) have reported that modification of the polyphosphate side chain of ATP along with substitution of the adenine moiety at the $C^2$-position, resulted in compounds that inhibited the $P2_T$ receptor (or $P2Y_{12}$ receptor). Zamecnik (U.S. Pat. No. 5,049,550) has disclosed a method for inhibiting platelet aggregation by administration of a diadenosine tetraphosphate-like compound, App($CH_2$)ppA. Kim and Zamecnik (U.S. Pat. No. 5,681,823) have disclosed $P^1, P^4$-(dithio)-$P^2,P^3$-(monochloromethylene)-5',5'''-diadenosine-$P^1,P^4$-tetraphosphate as an antithrombotic agent.

Nucleotide $P2Y_{12}$ antagonists have been developed, however, there is still a need for compounds that have improved oral bioavailability and blood stability.

Thienopyridines, ticlopidine and clopidogrel react covalently with the $P2Y_{12}$ receptor and produce irreversible platelet inhibition in vivo (Quinn and Fitzgerald, *Circulation* 100: 1667-1672 (1999); Geiger, et al., *Arterioscler. Thromb. Vasc. Biol.* 19: 2007-2011 (1999); Savi, et al., *Thromb Haemost.* 84: 891-896 (2000)). Patients treated with thienopyridines usually require 2-3 days of therapy to observe significant inhibition of platelet aggregation, however, and maximal inhibition usually is observed between 4 to 7 days after initiation of treatment. Also, the platelet inhibitory effect of thienopyridines persists up to 7-10 days after the therapy is discontinued, and both ticlopidine and clopidogrel produce a significant prolongation of the bleeding time (from 1.5 to 2-fold over control). Because of the prolonged effect of thienopyridines, these drugs need to be discontinued for 7 to 10 days prior to elective surgery, leaving the patient unprotected from a possible thrombotic event during that period. Recently, the association of thienopyridine treatment with events of thrombotic thrombocytopenic purpura has been reported (Bennett, et al., *N. Engl. J. Med.* 342: 1773-1777 (2000); Bennett, et al., *Ann. Intern. Med.* 128: 541-544 (1998)).

Derivatives of 5,7-disubstituted-1,2,3-triazolol[4,5-d]pyrimidin-3-yl-cyclopentanes and -tetrahydrofurans have been disclosed as antagonists of the P2T- (or $P2Y_{12}$) receptor on platelets (Cox, et al., U.S. Pat. No. 5,747,496, and related patents; Bonnert, et al., U.S. Pat. No. 6,297,232; WO 98/28300; Brown, et al., WO 99/41254; WO 99/05144; Hardern, et al. WO 99/05142; WO 01/36438; and Guile, et al. WO 99/05143) for use in the treatment of platelet aggregation disorders.

Guile, et al. (WO 00/04021) disclose the use of triazolo[4,5-d]pyrimidine compounds in therapy. Brown, et al. (U.S. Pat. No. 6,369,064) disclose the use of Triazolo(4,5-d)pyrimidine compounds in the treatment of myocardial infarction and unstable angina. Dixon, et al. (WO 02/096428) disclose the use of 8-azapurine derivatives in combination with other antithrombotic agents for antithrombotic therapy. Springthorpe discloses AZD6140 as a potent, selective, orally active $P2Y_{12}$ receptor antagonist which is now in Phase I clinical trials (Abstracts of Papers, 225th ACS National Meeting, New Orleans, La.; March, 2003; MEDI-016). WO 02/016381 discloses a method of preventing or treating diseases or conditions associated with platelet aggregation using mononucleoside polyphosphates and dinucleoside polyphosphates.

There is still a need in the areas of cardiovascular and cerebrovascular therapeutics, for selective, reversible inhibitors of platelet activation, which can be used in the prevention and treatment of thrombi or other aggregation-related problems. There is a need for potent and orally bioavailable compounds that can reversibly inhibit platelet aggregatation.

SUMMARY OF THE INVENTION

This invention is directed to methods of preventing or treating diseases or conditions associated with platelet aggregation or where the aggregation of platelets inhibits treatment options. This invention is directed to methods of preventing or treating thrombosis and related disorders.

The method comprises administering to a mammalian subject a composition comprising one or more non-nucleotide $P2Y_{12}$ receptor antagonist compound that effectively binds to $P2Y_{12}$ receptors on platelets, preferably in a reversible manner, and thereby causes an inhibition of the ADP-induced platelet aggregation response in blood or in a platelet-comprising material. The compounds useful for the methods are compounds of general Formula III, IIIa, or IIIb, and/or tautomers thereof, and/or pharmaceutically-acceptable hydrates, solvates, and/or salts thereof.

The invention also provides novel compounds and pharmaceutical compositions. The compounds of Formulae III, IIIa, and IIIb are useful in that they possess potent antagonist activity at platelet $P2Y_{12}$ receptors; they are chemically and biologically stable and have a good oral bioavailability.

Optionally, the compounds of this invention can be used in combination with other compounds useful for the treatment of platelet aggregation disorders or diseases.

DETAILED DESCRIPTION OF THE INVENTION

Definitions

When present, unless otherwise specified, the following terms are generally defined as, but are not limited to, the following:

Halo substituents are taken from fluorine, chlorine, bromine, and iodine.

Alkyl groups are from 1 to 12 carbon atoms inclusively, either straight chained or branched, are more preferably from 1 to 8 carbon atoms inclusively, and most preferably 1 to 6 carbon atoms inclusively.

Alkylene chains are from 2 to 20 carbon atoms inclusively, have two points of attachment to the to the molecule to which they belong, are either straight chained or branched, can contain one or more double and/or triple bonds, are more preferably from 4 to 18 atoms inclusively, and are most preferably from 6 to 14 atoms inclusively.

Alkenyl groups are from 1 to 12 carbon atoms inclusively, either straight or branched containing at least one double bond but can contain more than one double bond.

Alkynyl groups are from 1 to 12 carbon atoms inclusively, either straight or branched containing at least one triple bond but can contain more than one triple bond, and additionally can contain one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl- groups preferably having from 1 to 6 carbon atoms in the alkenyl moiety and from 6 to 10 carbon atoms inclusively in the aryl moiety.

"Arylalkynyl" refers to aryl-alkynyl-groups preferably having from 1 to 6 carbon atoms inclusively in the alkynyl moiety and from 6 to 10 carbon atoms inclusively in the aryl moiety.

"Aryloxy" refers to the group aryl-O— wherein the aryl group is as defined above including optionally substituted aryl groups as also defined above.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl -alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Heteroaryl" refers to a monovalent aromatic carbocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 carbon atoms inclusively in the heteroaryl moiety. Such arylalkyl groups are exemplified by pyridylmethyl and the like.

"Heteroarylalkenyl" refers to heteroaryl-alkenyl- groups preferably having from 1 to 6 carbon atoms inclusively in the alkenyl moiety and from 6 to 10 carbon atoms inclusively in the heteroaryl moiety.

"Heteroarylalkynyl" refers to heteroaryl-alkynyl-groups preferably having from 1 to 6 carbon atoms inclusively in the alkynyl moiety and from 6 to 10 carbon atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Positions occupied by hydrogen in the foregoing groups can be further substituted with substituents exemplified by, but not limited to, hydroxy, oxo, nitro, methoxy, ethoxy, alkoxy, substituted alkoxy, fluoro, chloro, bromo, iodo, methyl, ethyl, propyl, butyl, alkyl, substituted alkyl, thio, thioalkyl, acyl, carboxyl, alkoxycarbonyl, carboxamido, substituted carboxamido, alkylsulfonyl, alkylsulfinyl, alkylsulfonylamino, sulfonamido, substituted sulfonamide, cyano, amino, substituted amino, acylamino, trifluoromethyl, trifluoromethoxy, phenyl, aryl, substituted aryl, pyridyl, imidazolyl, heteroaryl, substituted heteroaryl, cyclopropyl, cyclobutyl, cyclopentyl, cyclohexyl, cycloalkyl, substituted cycloalkyl, pyrrolidinyl, piperidinyl, morpholino, and heterocycle; and preferred heteroatoms are oxygen, nitrogen, and sulfur. It is understood that where open valences exist on these substituents they can be further substituted with alkyl, cycloalkyl, aryl, heteroaryl, and/or heterocycle groups, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

Tautomers are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N, N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

$P2Y_{12}$ Receptor Antagonist Compounds $P2Y_{12}$ receptor antagonist compounds useful for preventing or treating diseases or conditions associated with platelet aggregation and/or platelet activation include compound of general Formula III, and/or tautomers thereof, or a pharmaceutically acceptable salt, solvate, or hydrate thereof:

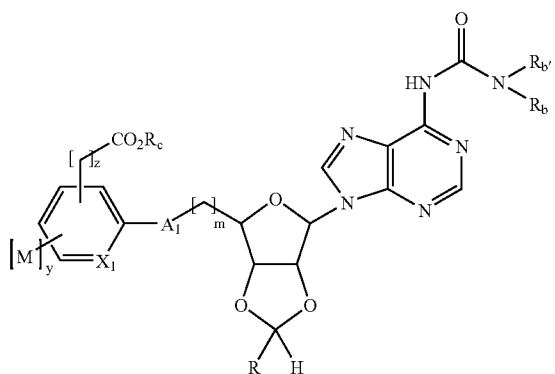

Formula III wherein:

$R_a$ is selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aralkenyl, aralkynyl, aryl, and saturated or unsaturated $C_{3-6}$ heterocycle; where all rings or chains optionally can bear one or more desired substituents;

$R_b$ and $R_{b'}$ are independently selected from the group consisting of: H, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aralalkyl, aralkenyl, aralkynyl, aryl, heteroaryl, and saturated or unsaturated $C_{3-6}$ heterocycle; or $R_b$ and $R_{b'}$ groups are taken together to form a ring of 4 to 7 members, with or without unsaturation and with or without heteroatoms in place of ring-carbon units;

$X_1$ is C or N;

$R_c$ is H, a physiologically-relevant cation forming a carboxylate salt, alkyl, aryl, or aralkyl, with the resultant moiety $C(O)OR_c$ preferably having an adjacent relationship to the attachment point of $A_1$; preferably $R_c$ is H or alkyl (such as ethyl);

$z=0-2$;
$m=1-2$;
$A_1$ is O or $CH_2$;

M is selected from the group consisting of: halogen (such as F, Cl, Br), —$CF_3$, $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, aralkenyl, aralkynyl, heteroaryl, saturated or unsaturated $C_{3-6}$ heterocycle, —OH, cyano, nitro, saturated or unsaturated $C_{1-6}$ alkoxy, aralkoxy, aryloxy, —SH, $C_{1-6}$ thioalkyl, thioaryl, —[(CO)OR'], —[(CO)NR'R"], amino, —N-substituted amino, N,N-disubstituted amino, and the like;

wherein each said substituent R' or R" is independently selected from the group consisting of: H, a physiologically-relevant cation forming a carboxylate salt (when the moiety is —[(CO)OR']), $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, aralkenyl, aralkynyl, heteroaryl, or $C_{3-6}$ heterocycle; and $y=0-4$, with the proviso that the resultant structure is chemically reasonable, such that more than one moiety M can be present, either the same or different; and substituent or substituents M may occupy any of the available positions on the ring not already occupied by the moiety that comprises $CO_2R_c$; and any positions on the ring not occupied by M or the moiety that comprises $CO_2R_c$ is understood to be H, whether stated or not, as long the resulting structure is chemically reasonable; and with the proviso that when $X_1$ is N, the nitrogen atom bears no substituent.

Preferably, the furanosyl moiety in Formula III has the 2'- and 3'-oxygen-groups in a cis-orientation relative to one another on the furanose ring. Preferred furanosyl moiety is derived from ribose; however, other furanose derivatives can also be used. A preferred stereochemical embodiment of this invention includes, but is not limited to (D)-ribose-(2',3'-acetal) compounds of Formula III, such as found in acetals derived from (–)-adenosine.

In one embodiment of the present invention, the acetal carbon bearing $R_a$ and a hydrogen atom is chiral, making the compounds either in a pure form of one of the two possible diastereomers, or as a mixture of the two diastereomers in any proportion. As a practical matter, the compounds as depicted here represent the pure forms of the diastereomers. Diastereomers are distinct compounds, each with potentially different chemical and biological properties; thus pure forms are preferred as pharmaceutical agents. In addition, there are generally reasons, including but not limited to, the ease of chemical synthesis or separation, chemical or biological stability, toxicity, pharmacokinetic or pharmacodynamic properties in living systems, and the like, to choose between the two possible isomers. While it is possible to resolve such diastereomeric mixtures using chiral chromatographic methods, it is more preferred to synthesize a single diastereomer.

Depending on the acetal in question, the synthesis of a single diastereomer can be achieved in several ways. In some cases, one diastereomer can be selectively generated over the other by carrying out the acetal-forming reaction at a low temperature (such as below 0° C., for example, from –10 to –30° C.). In other cases, a mixture of two diastereomers having different acetal stabilities can be subjected to aqueous acidic conditions, which leads to decomposition of the less-stable diastereomer, while leaving the more stable diastereomer intact. In general, the single diastereomer that survives the decomposition is preferred, since chemical stability is an important attribute for a pharmaceutical product.

For molecules base on a ribose core, an important aspect of this acetal modification is that the resultant bicyclic structure (i.e. the bicyclic ring system arising from the fusion of the ribose residue and acetal ring at the 2' and 3' carbons of the ribose) is much more stable compared with the native nucleoside structure where the 2' and 3' hydroxyl groups are free. As a result, the chemical and biological degradation processes that nucleosides with free 2' and 3' hydroxyls typically undergo are reduced, thus the stability of the compound is improved. High overall chemical and biological stability are important attributes for pharmaceutical products, especially for those being designed for chronic treatment delivered via oral administration, where the pharmaceutical product will be subject to a broad range of chemical and biological environments.

Another aspect of the acetal modification is that it provides and/or enhances the $P2Y_{12}$ antagonist properties to the molecules so modified. In general, removal of the acetal functionality from the compounds of the present invention substantially diminishes or completely abolishes the activity at $P2Y_{12}$. As a result, the discovery of the $P2Y_{12}$ antagonist properties conferred by the acetal modification to the ribose core of a nucleoside is one important feature of the compounds of the present invention.

When Ra contains an aromatic ring, the aromatic ring is optionally substituted with various substituents. These substituents can be chosen to enhance the pharmaceutical properties of the molecules of interest. For example, replacement of a hydrogen atom on the phenyl ring of an aromatic acetal with fluorine can be done to prevent hepatic metabolism at that position following in vivo administration of the compound. Alternately, replacement of a hydrogen atom on the phenyl ring with a basic or acidic moiety can be done to improve the solubility of the molecules of interest, or to enhance the ability of the compound to be absorbed from the digestive tract when given orally. Alternately, a hydrogen atom on the phenyl ring can be replaced with a moiety that will be metabolized in a predictable fashion, leading to an active form of the compound in vivo, or leading to a species that has a preferred mode of excretion. These modifications to the phenyl ring of an aromatic acetal are given to illustrate, not to limit, ways that substituents can positively affect the pharmaceutical properties of a compound of the present invention. Other modifications can also be envisioned to improve various aspects of the pharmaceutical properties of said compounds. A preferred modification to the phenyl ring of an aromatic acetal is fluorine substitution, for example, p-fluorophenyl acetal.

The ring which includes $X_1$ is either a phenyl ring ($X_1$=C) or a pyridine ring ($X_1$=N). Potent compounds of the present invention have a carboxylic acid or carboxymethylene moiety as a substituent on either the phenyl or pyridine ring. The inventors unexpectedly found that the more potent compounds in the series were those where the carboxylic acid or carboxymethylene group was located in an ortho relationship to the attachment point of $A_1$, as opposed to those where the carboxylic acid or carboxymethylene moiety was located in either a meta or para relationship to $A_1$. In general, compounds with a phenyl ring bearing such an ortho carboxyl group or ortho carboxymethylene group are preferred over the analogous pyridine compounds, as the former are typically more potent and present fewer synthetic challenges than the latter.

Preferred Formula III compounds are those wherein $A_1$ is O (phenyl ether), m=1, and the carboxylic moiety is at an ortho position (Formula IIIa) or the carboxymethylene moiety is at an ortho position (Formula IIIb):

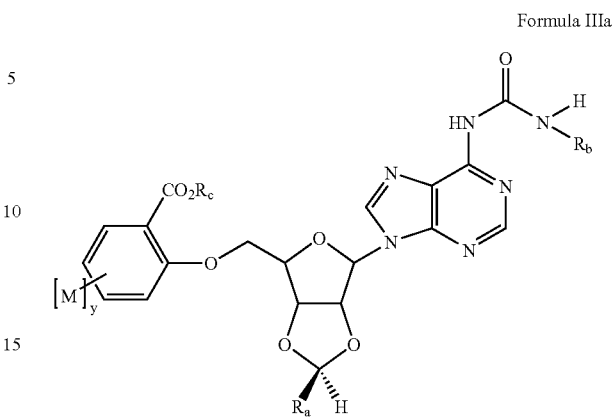

Formula IIIa wherein:
$R_b$=$C_{1-8}$ alkyl (preferably $C_{1-5}$ alkyl or $C_{1-4}$ alkyl), $C_{3-6}$ cycloalkyl, or $C_{3-6}$ alkylcycloalkyl, with 1-2 carbons in the alkyl portion;
$R_a$=trans-p-fluorophenyl, or trans-styryl; where trans refers to the configuration of hydrogen atom on the acetal carbon of the dioxolane ring relative to the hydrogens on the 2' and 3' carbons of the ribose ring, as depicted in Formula IIIa;
$R_c$ is H, a physiologically-relevant cation forming a carboxylate salt, or alkyl;
M=hydrogen, halogen, $C_{1-4}$ alkyl, or $C_{1-4}$ alkoxy; and
y=1 or 2.

Formula IIIb wherein:
$R_b$=$C_{1-8}$ alkyl (preferably $C_{1-5}$ alkyl or $C_{1-4}$ alkyl), $C_{3-6}$ cycloalkyl, or $C_{3-6}$ alkylcycloalkyl, with 1-2 carbons in the alkyl portion;
$R_a$=trans-p-fluorophenyl, or trans-styryl; where trans refers to the configuration of hydrogen atom on the acetal carbon of the dioxolane ring relative to the hydrogens on the 2' and 3' carbons of the ribose ring, as depicted in Formula IIIb;
$R_c$ is H, a physiologically-relevant cation forming a carboxylate salt, or alkyl;
M=hydrogen, halogen, $C_{1-4}$ alkyl, or $C_{1-4}$ alkoxy; and
y=1 or 2.

For compounds of the present invention falling under the definitions of Formulae IIIa and IIIb, the configuration of the acetal carbon is trans. This configuration places the group $R_a$ "up" relative to the plane of the acetal 1,3-dioxolane ring, and the hydrogen atom on the acetal carbon "down" relative to the dioxolane ring. The trans configuration is a key aspect of the compounds of the present invention, as it provides for compounds with high P2Y$_{12}$ antagonist potency and greatly enhanced chemical stability relative to the corresponding analogs where the configuration is cis.

Applicants have unexpectedly found that compounds falling under the definition of Formulae IIIa and IIIb, where the oxygen atom is directly bound to the phenyl ring and the linker between the ribose ring and the phenyl ring is only 2 atoms are potent and orally bioavailable. Synthesis of these compounds containing a phenyl ether moiety is conveniently carried out by a number of chemical processes known to those skilled in the art. Particularly useful for this purpose are alkylation reactions, as these reactions typically proceed in good yield and allow for diverse product structures, owing to the wide variety of alkylation reagents which are commercially available. Such phenyl ethers can be synthesized using the well known Mitsunobu Reaction, which allows for electrophilic activation of the 5' hydroxyl group of the nucleoside, followed by coupling with acidic reagents such as carboxylic acids or phenols. When phenols bearing substituents are used, the phenyl ethers which are the subject of the present invention can be synthesized. This retention of potent activity in the phenyl ether series and their good metabolic stability are key aspects of the preferred compounds of the present invention. In vitro biological data for representative compounds in this molecular series is presented in Table 1.

Formula IIIa and Formula IIIb compounds are highly potent, and a substantial amount of the compounds are absorbed following oral administration. The high oral bioavailability, coupled with the good chemical and biological stability of the compounds, makes the compounds of the present invention highly suitable for applications where inhibition of platelet aggregation by an orally-delivered drug is desired.

Some of the preferred compounds falling under the definition of Formulae IIIa and IIIb are:

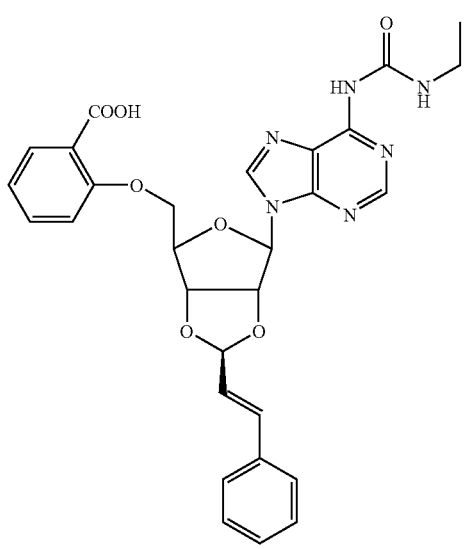

1

-continued

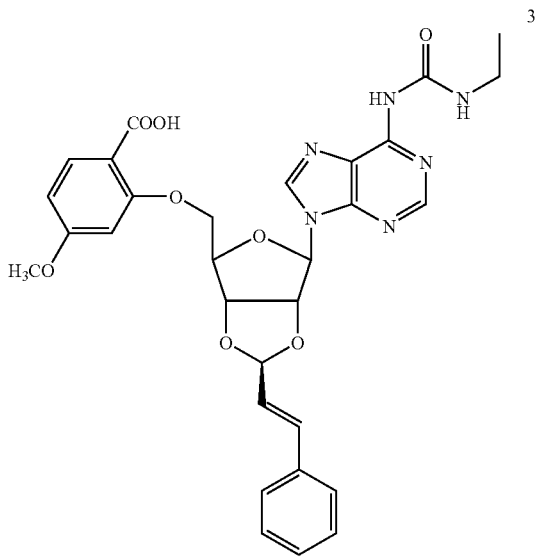

2

3

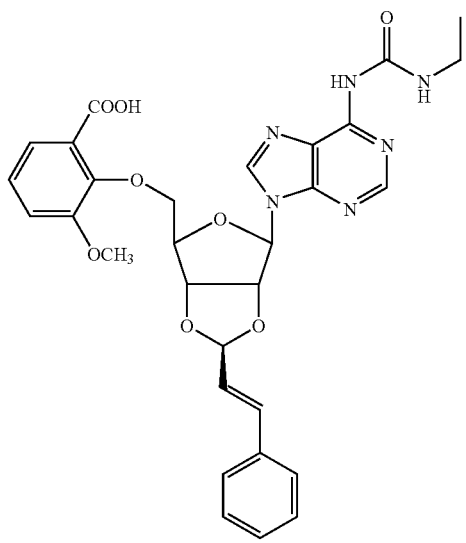

4

5
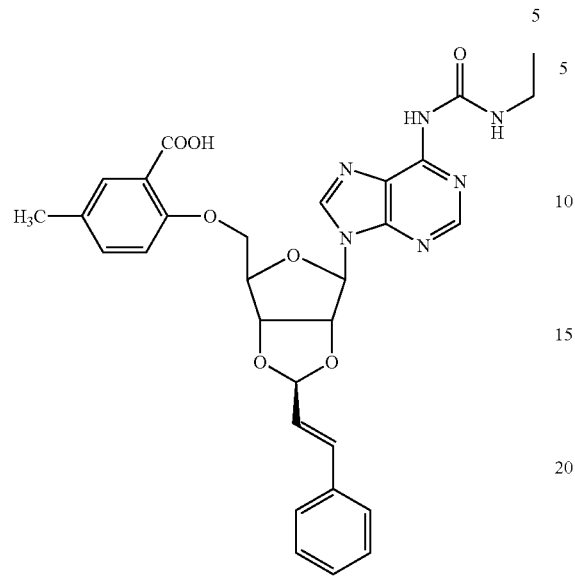
6
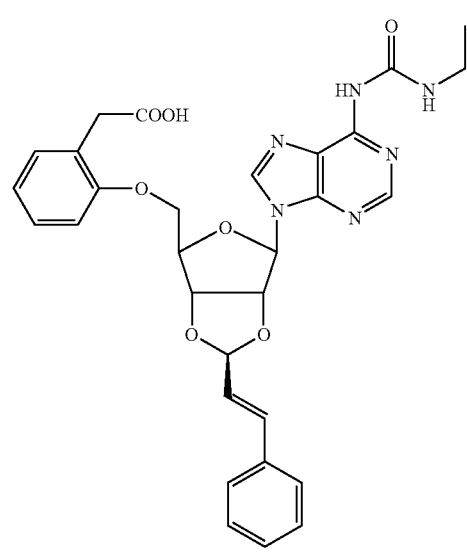
7
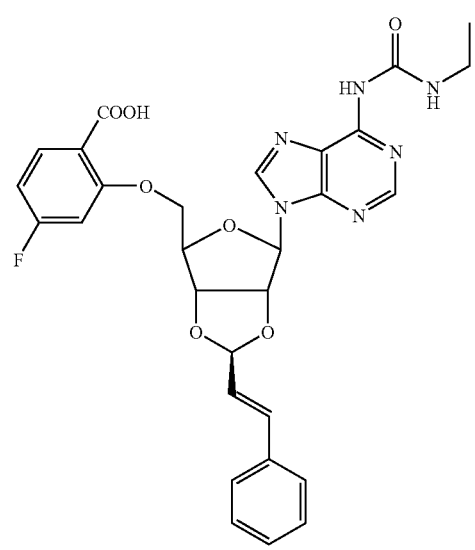
8
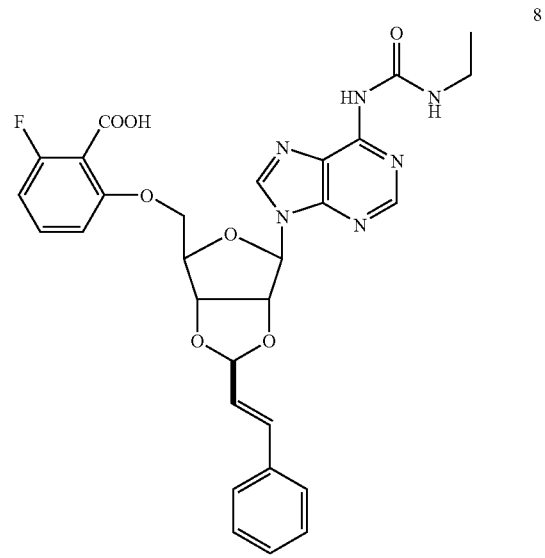
9
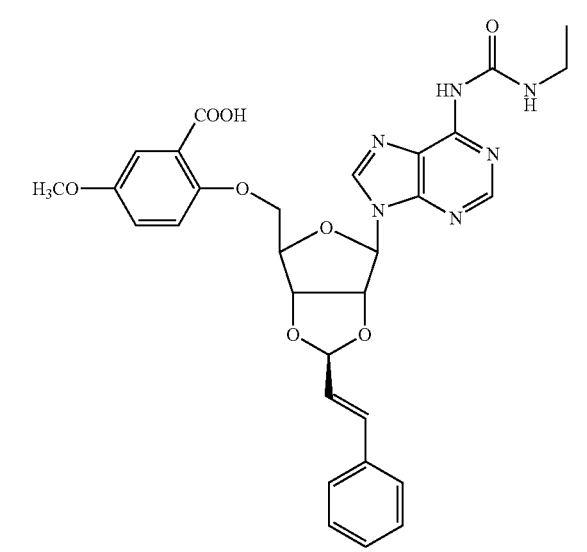
10
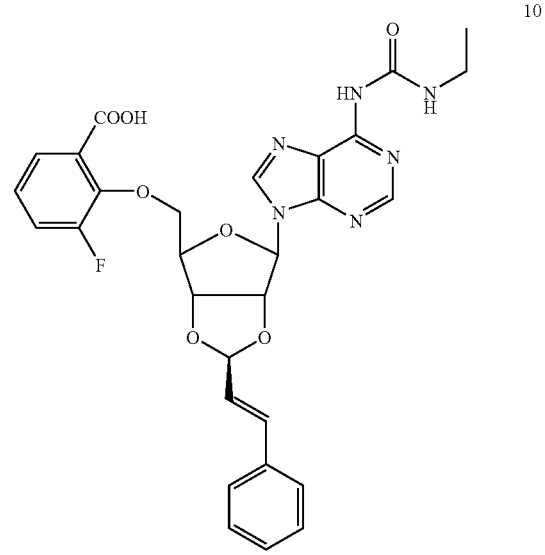

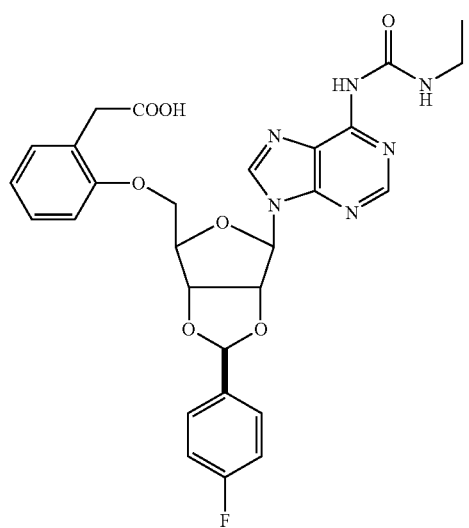
11
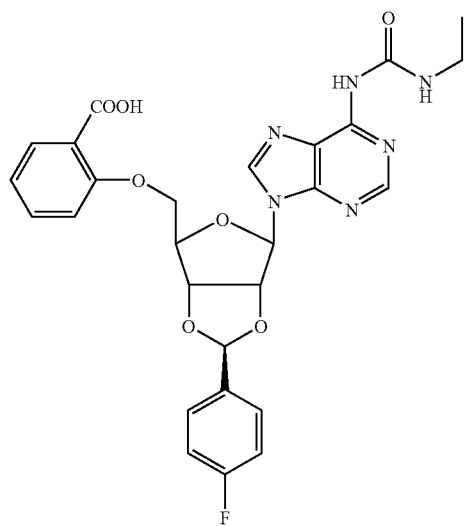
12
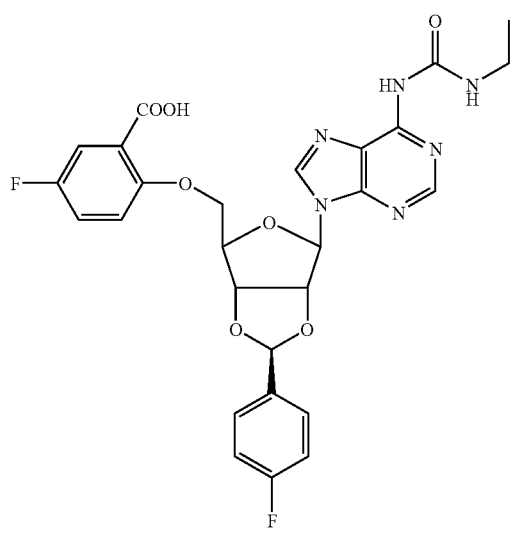
13
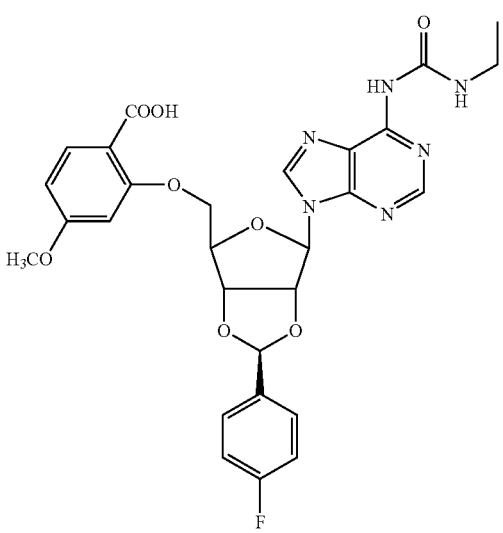
14
15
16

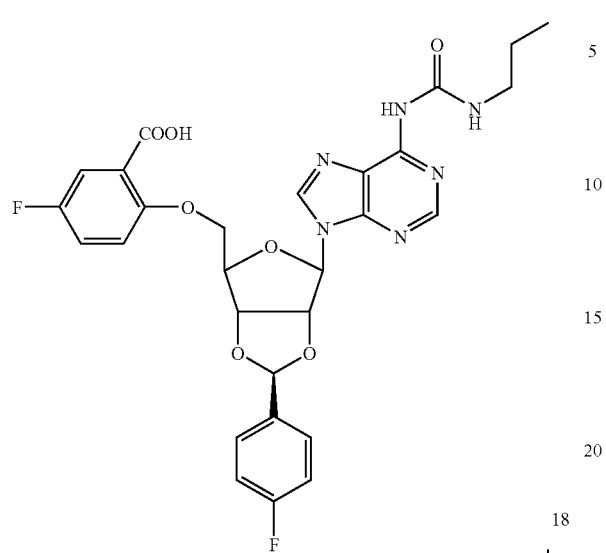
17
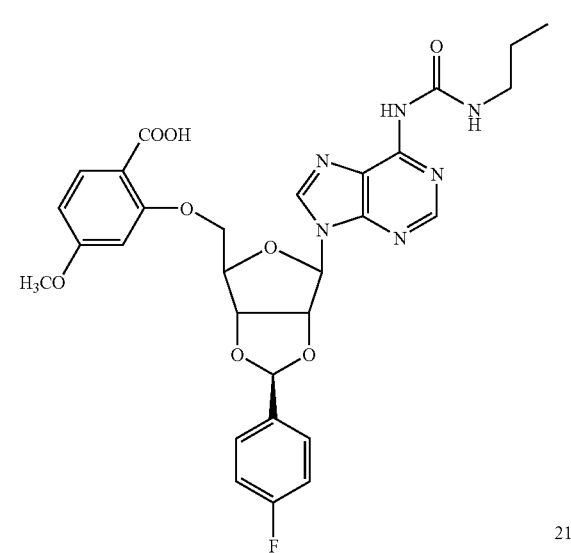
20
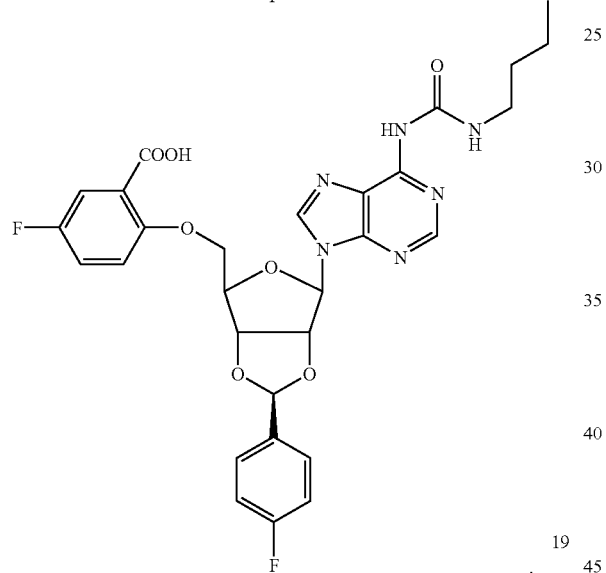
18
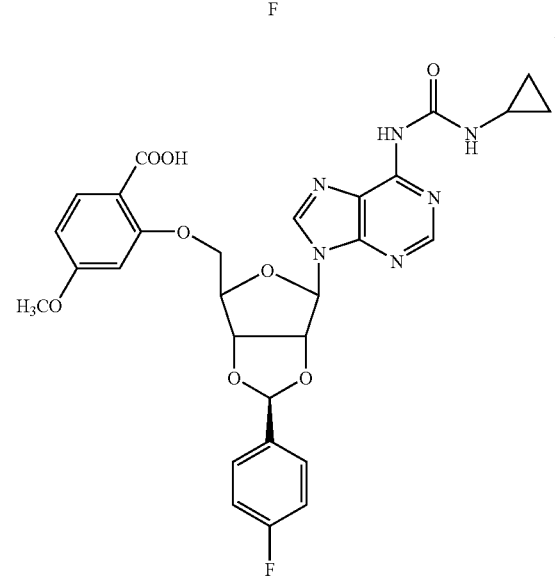
21
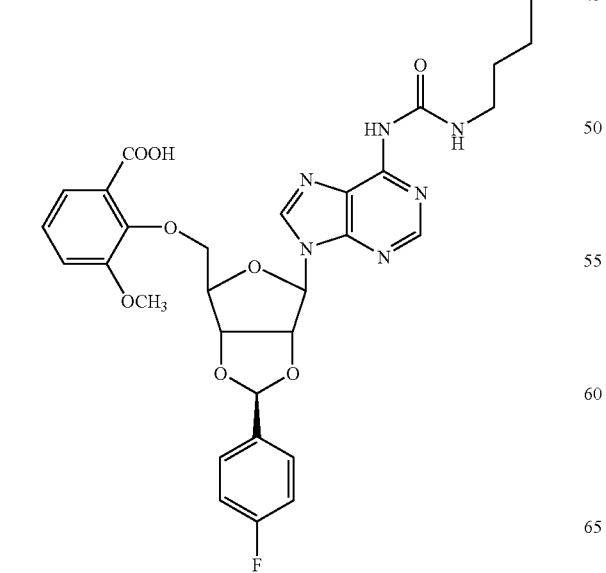
19
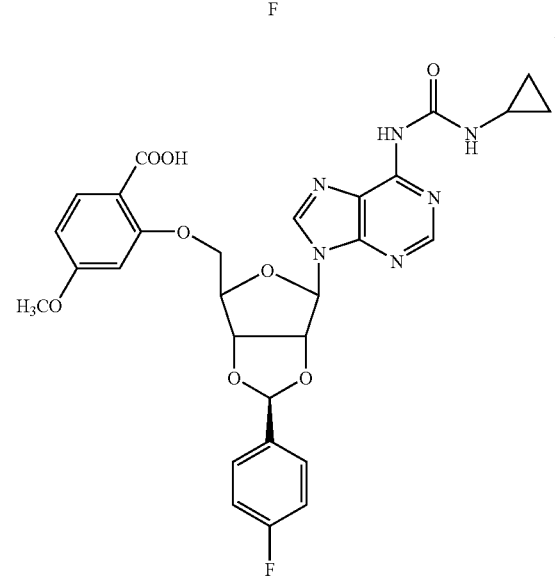
22

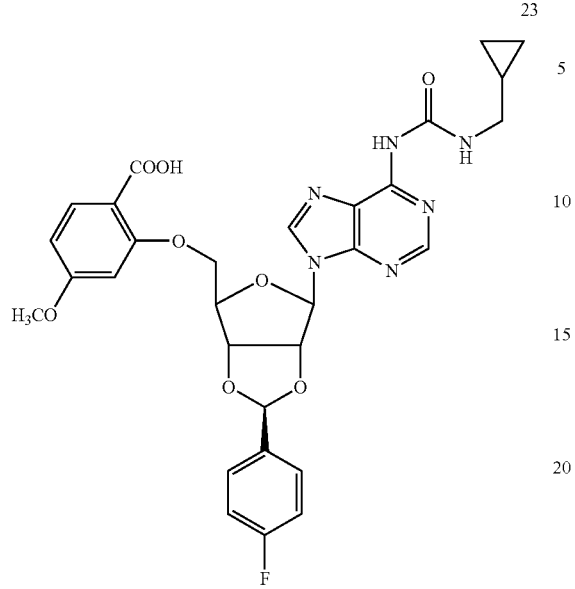
23
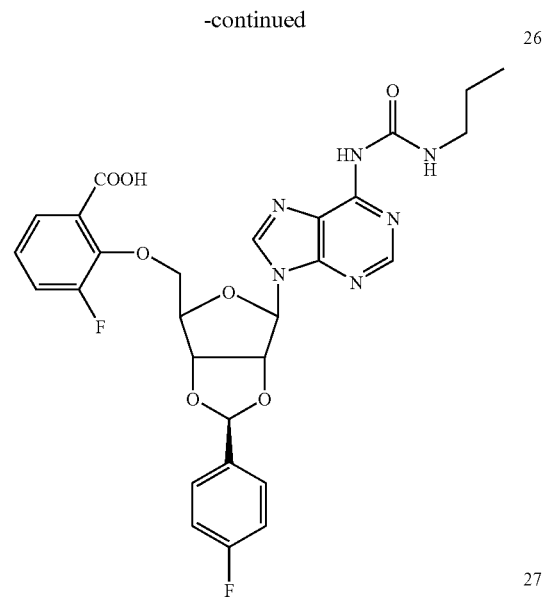
26
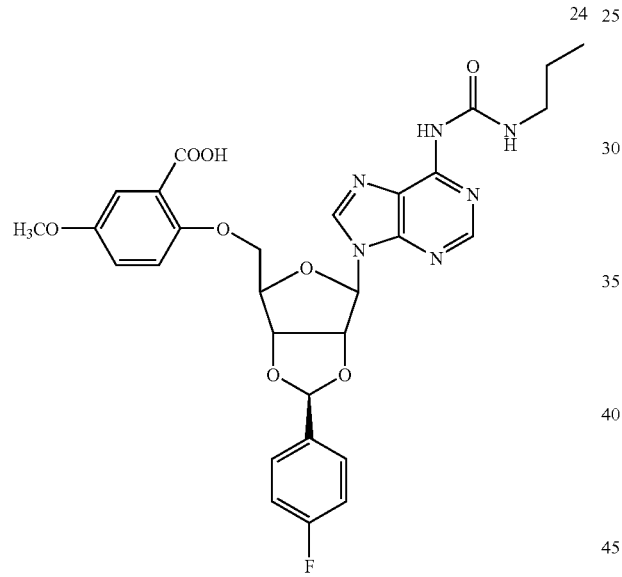
24
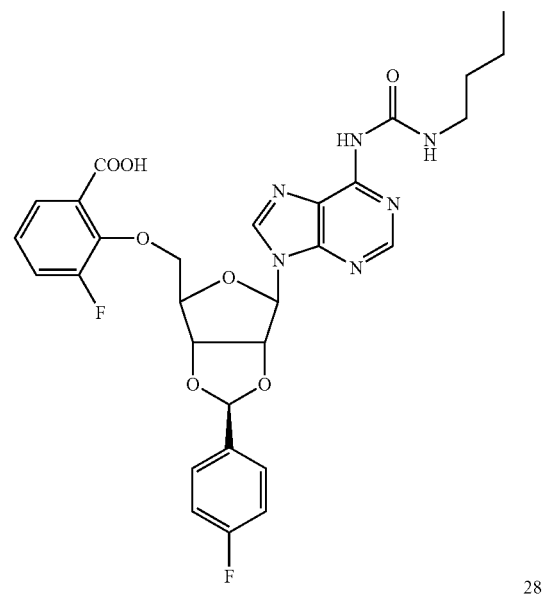
27
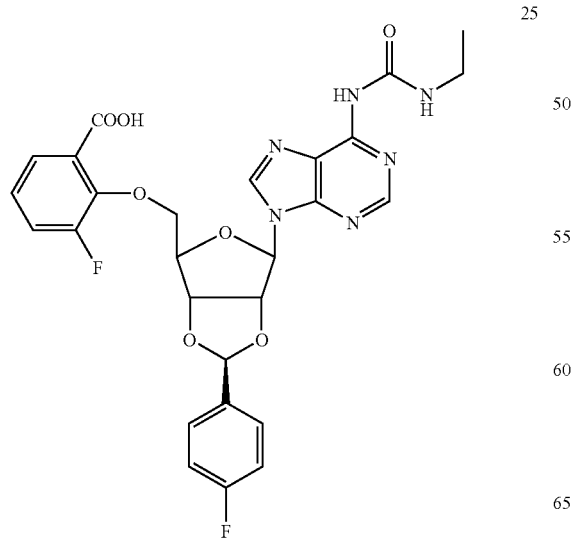
25
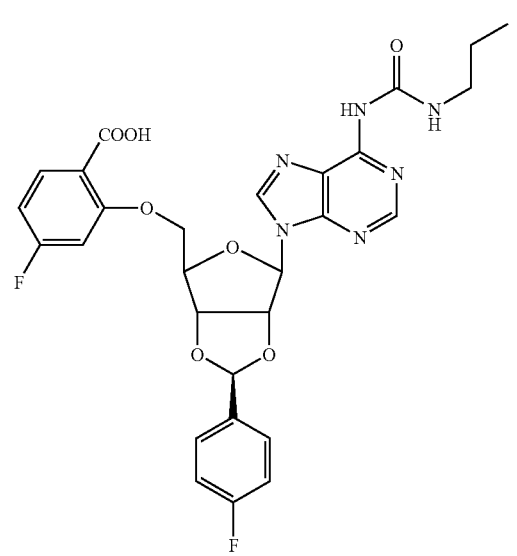
28

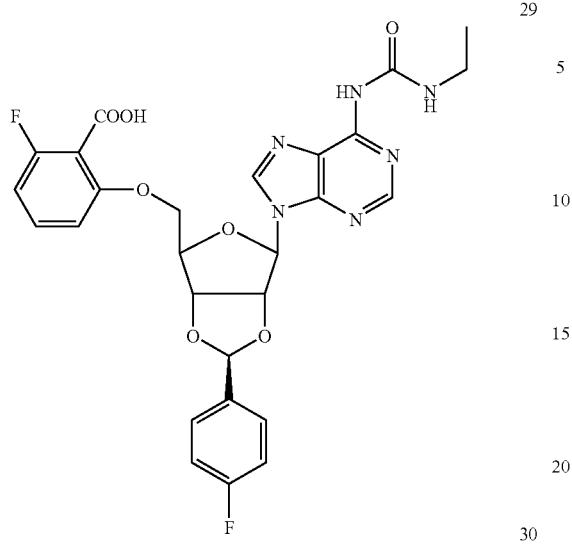
29
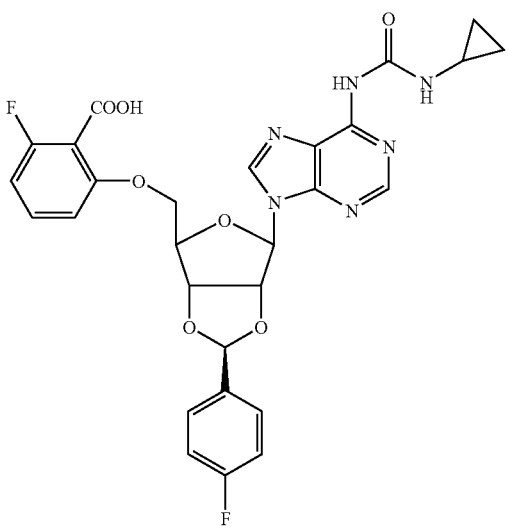
32
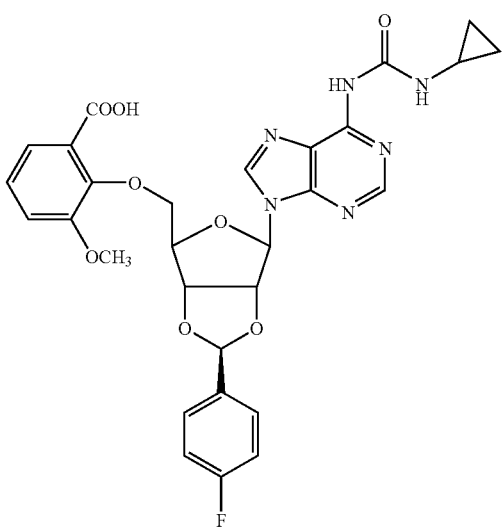
33
30
31
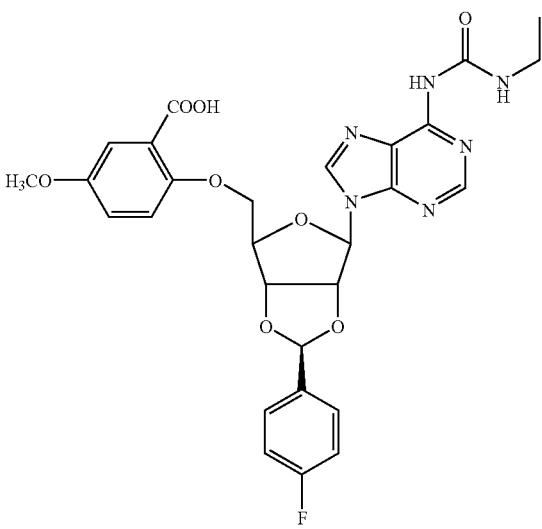
34

-continued

35

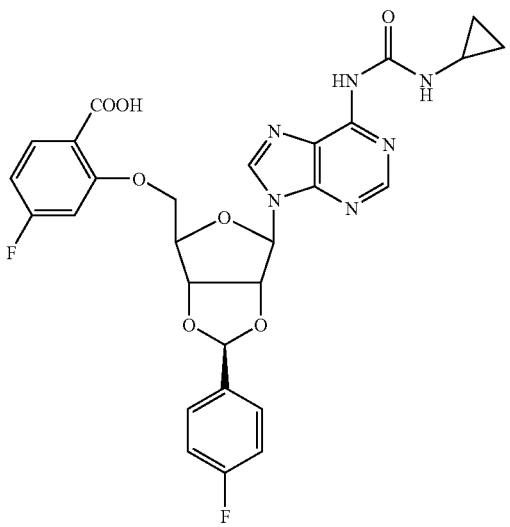

Pharmaceutical Formulations

The present invention additionally provides novel pharmaceutical formulations comprising a pharmaceutically acceptable carrier and compounds of Formula III, IIIa, IIIb, or a pharmaceutically acceptable salt, solvate, or hydrate thereof. Pharmaceutically acceptable carriers can be selected by those skilled in the art using conventional criteria. Pharmaceutically acceptable carriers include, but are not limited to, saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation of the present invention provides an aqueous solution comprising water, suitable ionic or non-ionic tonicity modifiers, suitable buffering agents, and a compound of Formula III. In one embodiment, the compound is at 0.005 to 3% w/v, and the aqueous solution has a tonicity of 200-400 mOsm/kG and a pH of 4-9.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to intravenous administration.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 3.5-5%, and more preferably 4.2-5% w/v.

Those skilled in the art will recognize various synthetic methodologies that may be employed to prepare non-toxic pharmaceutically acceptable salts and prodrugs of the compounds.

Use of $P2Y_{12}$ Receptor Antagonist Compounds

This invention provides a method of preventing or treating diseases or conditions associated with platelet aggregation and/or platelet activation. This invention also provides a method for solving treatment problems or limited treatment options caused by the aggregation of platelets or by the irreversible inhibition of platelet aggregation.

This invention provides methods of preventing or treating thrombosis and related disorders, such as venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions. This invention further provides methods for the prevention of embolism or thrombosis during percutaneous coronary interventions, placement of coronary stents, coronary angioplasty, coronary endarectomy, carotid endarectomy, or due to platelet-aggregation complications related to atherosclerosis, inflammation, exposure of blood to artificial devices, drug effects.

This invention further provides methods of inhibiting platelet aggregation in blood and blood products comprising platelets, such as stored blood.

The method comprises administering to a subject or blood and blood products a composition comprising an effective amount of $P2Y_{12}$ receptor antagonist compound, wherein said amount is effective to bind the $P2Y_{12}$ receptors on platelets and inhibit platelet aggregation, preferably in a reversible manner.

The invention further provides useful methods of treating patients to inhibit platelet aggregation in a reversible manner, especially in patients that are subject to a procedure such as percutaneous coronary interventions, stent placement, balloon angioplasty, coronary atherectomy, coronary endarterectomy, carotid endarterectomy, thrombolytic theraphy, coronary or other vascular graft surgery, dialysis, etc. In those patients, it is important that platelet aggregation inhibition can be rapidly reversed (within hours for oral administration and within minutes for intravenous administration) if necessary. The method comprises the steps of: (a) providing a patient in need of rapid reversal of platelet aggregation inhibition; (b) administering a therapeutically effective amount of a compound of Formula III to the patient; (c) submitting the patient to a procedure selected from the group consisting of: percutaneous coronary interventions, stent placement, balloon angioplasty, coronary atherectomy, coronary endarterectomy, carotid endarterectomy, thrombolytic theraphy, coronary or other vascular graft surgery, and dialysis, (d) discontinuing the administering of said compound to the patient; and (e) allowing the amount of said compound in the patient's blood to reduce to below an therapeutically effective amount. In step (b), the administration of the compound can be either continuous or intermittent as long as it provides a therapeutically effective amount of the compound in the patient's blood. The amount of the compound in the patient's blood is monitored.

The compounds of general Formula III, IIIa, and IIIb are antagonists of the effect of ADP on its platelet membrane receptor, the $P2Y_{12}$ receptor. The compounds of general Formula III, IIIa, and IIIb are useful in therapy, in particular in the prevention or treatment of platelet aggregation. The compounds provide efficacy as antithrombotic agents by their ability to block ADP from acting at its platelet receptor site and thus prevent platelet aggregation. The compounds provide a more efficacious antithrombotic effect than aspirin, but with less profound effects on bleeding than antagonists of the fibrinogen receptor.

The $P2Y_{12}$ receptor antagonists of this invention, in contrast with currently available marketed products clopidogrel (PLAVIX®) and ticlopidine (TICLID®), bind to the $P2Y_{12}$ receptor in a reversible fashion and therefore, the effects of the treatment with compounds described in this invention are reversed by the simple discontinuation of the treatment, restoring the hemostatic functionality of the platelet as necessary. Since platelets are non-nucleated cell particles that lack the ability to synthesize new proteins, treatment of subjects with irreversible $P2Y_{12}$ antagonists results in the impairment of platelet function that lasts for the lifespan of the platelet (approximately 8 to 10 days). The use of irreversible $P2Y_{12}$ antagonists such as clopidogrel has been associated with increases in blood loss, transfusion requirements and rate of reoperation after cardiac surgery (Kapetanakis, et al., *Eur Heart J.* 26: 576-83, 2005). To avoid these complications, subjects undergoing elective surgeries are required to discontinue the treatment with irreversible antagonists for at least five days prior to the surgery, which increases the risk of a thrombotic event during this period. Therefore, the compounds described in this invention represent an advantage over the currently marketed compounds.

The ADP-induced platelet aggregation is mediated by the simultaneous activation of both $P2Y_{12}$ and $P2Y_1$ receptors, thus the combined administration of the Formula III compounds with antagonists of platelet $P2Y_1$ receptors can provide a more efficacious antithrombotic effect at concentrations of each antagonist that are below the effective concentrations to block each receptor subtype in other systems, resulting in a decrease of the potential manifestation of adverse effects. In addition, these compounds can be used in conjunction with lower doses of other platelet aggregation inhibitors, which work by different mechanisms, to reduce the possible side effects of said agents.

The compounds of the present invention are useful as antithrombotic agents, and are thus useful in the treatment or prevention of unstable angina, coronary angioplasty (PTCA) and myocardial infarction.

The compounds of the present invention are useful in the treatment or prevention of primary arterial thrombotic complications of atherosclerosis such as thrombotic stroke, peripheral vascular disease, and myocardial infarction without thrombolysis.

The compounds of the invention are useful for the treatment or prevention of arterial thrombotic complications due to interventions in atherosclerotic disease such as angioplasty, endarterectomy, stent placement, coronary and other vascular graft surgery.

The compounds of the invention are useful for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are useful for the prevention of mechanically-induced platelet activation in vivo, for example, caused by cardiopulmonary bypass, which results in temporary platelet dysfunction (prevention of microthromboembolism). The compounds of the present invention are useful for prevention of mechanically-induced platelet activation in vitro. For example, the compounds are useful in the preservation of blood products, e.g. platelet concentrates, prevention of shunt occlusion such as renal dialysis and plasmapheresis, and thrombosis secondary to vascular damage/inflammation such as vasculitis, arteritis, glomerulonephritis and organ graft rejection.

The compounds of the present invention are useful in disorders with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

The compounds of the invention are useful for the treatment or prevention of venous thrombosis such as deep vein thrombosis, veno-occlusive disease, hematological conditions such as thrombocythemia and polycythemia, and migraine.

The compounds of the present invention are useful in treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of the present invention are useful in treating chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment.

The compounds of the present invention are useful in treating diseases or conditions associated with platelet activation and/or aggregation produced by the contact of blood with an artificial device. In one embodiment, the artificial device is a paracorporeal artificial lung and an extracorporeal membrane oxigenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

Additionally, if the compounds of the present invention have sufficient binding affinity and bear a fluorescent moiety, they are useful as biochemical probes for the $P2Y_{12}$ receptor.

In a preferred embodiment, the compounds are used in the treatment of unstable angina, coronary angioplasty and myocardial infarction.

In another preferred embodiment, the compounds are useful as adjunctive therapy in the prevention or treatment of thrombotic disorders, such as coronary arterial thrombosis during the management of unstable angina, coronary angioplasty and acute myocardial infarction, for example, as adjuvants of thrombolytic therapy. The compounds are also administered in combination with other antiplatelet and/or anticoagulant drugs such as heparin, aspirin, GP IIIb/IIIa antagonists, or thrombin inhibitors.

This invention provides a method of inhibiting platelet aggregation and clot formation in a mammal, especially a human, which comprises administering to the subject a compound of Formula III, IIIa, or IIIb, and a pharmaceutically acceptable carrier.

This invention further provides a method for inhibiting the reocclusion of an artery or vein and the formation of new blood clots following fibrinolytic therapy, which comprises administering to a subject a compound of Formula III, IIIa, or IIIb, and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule. The increased clinical efficacy of the combination of the compounds described in this invention with fibrinolytic agents allows the use of lower concentrations of the fibrinolytic agent, which decreases the risk of hemorrhagic events. This in turn, allows the administration of fibrinolytic therapy over an extended period of time after a heart attack or stroke.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The active compounds can be administered systemically to target sites in a subject in need such that the extracellular concentration of a $P2Y_{12}$ agonist is elevated to block the binding of ADP to $P2Y_{12}$ receptor, thus inhibit the platelet aggregation. The term systemic as used herein includes subcutaneous injection, intravenous, intramuscular, intrastemal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation can be a sterile indictable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases $P2Y_{12}$ antagonists in a sustained capacity. Intravitreal delivery can also include delivery during surgical manipulations as either an adjunct to the intraocular irrigation solution or applied directly to the vitreous during the surgical procedure.

For systemic administration, plasma concentrations of active compounds delivered can vary according to compounds; but are generally $1 \times 10^{-10} - 1 \times 10^{-4}$ moles/liter, and preferably $1 \times 10^{-8} - 1 \times 10^{-5}$ moles/liter.

The pharmaceutical utility of $P2Y_{12}$ antagonist compounds of this invention is indicated by their inhibition of ADP-induced platelet aggregation. This widely used assay, as described in S. M. O. Hourani et al. Br. J. Pharmacol. 105, 453-457 (1992) relies on the measurement of the aggregation of a platelet suspension upon the addition of an aggregating agent such as ADP.

The invention is illustrated further by the following examples that are not to be construed as limiting the invention in scope to the specific procedures described in them.

EXAMPLES

Example 1

Preparation of 2-[6-[6-(3-Ethyl-ureido)-purin-9-yl]-2-(4-fluoro-phenyl)-tetrahydro-furo[3,4-d][1,3]dioxol-4-ylmethoxyl]-4-methoxy-benzoic acid (14)

a. 9-[6-(tert-Butyl-dimethyl-silanyloxymethyl)-2-trans-(4-fluoro-phenyl)-tetrahydro-furo[3,4-d][1,3]dioxol-4-yl]-9H-purin-6-ylamine (prepared from adenosine by sequential 2',3'-acetal formation using p-fluorobenzaldehyde/trifluoroacetic acid, cleavage of the less stable cis acetal isomer with aqueous acid, and protected at the 5' position with t-butyldimethylsilyl chloride/imidazole/DMF; 7.00g, 14.4 mmol) was suspended in toluene (50 mL) in a Parr bomb and ethyl isocyanate (11.3 mL, 144 mmol) added. The mixture was heated for 12 hrs at 90° C., at which point the reaction was complete by LCMS. The volatiles were removed under vacuum and the crude product was used without purification in the next step.

b. 1-{9-[6-(tert-Butyl-dimethyl-silanyloxymethyl)-2-(4-fluoro-phenyl)-tetrahydro-furo[3,4-d][1,3]dioxol-4-yl]-9H-purin-6-yl}-3-ethyl-urea (8.01, 14.3 mmol) from the previous step was dissolved in THF (100 mL) and tetra-n-butylammonium fluoride (1 M in THF, 22 mL, 22 mmol) added. The reaction was stirred for 1 hr, after which the solvent was removed by evaporation. The mixture was diluted with acetonitrile (50 mL) and water added to precipitate the product. After filtration and drying, the product (about 5.5 g, ca. 86% yield) was carried into the next step.

c. Triphenylphosphine (4.9 g, 18.7 mmol) and dichloromethane (56 mL) were combined and cooled to 0-5° C. Diisopropyl azodicarboxylate (3.32 mL, 16.9 mmol) was added dropwise and the mixture stirred for 5 min in the cold. 1-Ethyl-3-{9-[2-(4-fluoro-phenyl)-6-hydroxymethyl-tetrahydro-furo[3,4-d][1,3]dioxol-4-yl]-9H-purin-6-yl}-urea (3.00 g, 6.75 mmol) from the previous step was added, followed by methyl 2-hydroxy-4-methoxybenzoate (3.07 g, 16.9 mmol) and the yellow mixture stirred for 2 days at ambient temperature. The product was isolated by prep HPLC ($C_{18}$; gradient from 0.025 M $NH_4OAc$ to acetonitrile), lyophilized (giving 2.8 g, 68% yield), and used directly in the next step.

d. 2-[6-[6-(3-Ethyl-ureido)-purin-9-yl]-2-(4-fluoro-phenyl)-tetrahydro-furo[3,4-d][1,3]dioxol-4-ylmethoxy]-4-methoxy-benzoic acid methyl ester (2.68 g, 4.4 mmol) from the previous step was dissolved in THF (35 mL), and a solution of lithium hydroxide monohydrate (0.554 g, 13.2 mmol) in water (0.635 mL, 35.2 mmol) added. The reaction was stirred for 3 days at ambient temperature, at which point LCMS indicated that the hydrolysis was 90% complete. The base was quenched with acetic acid and the product extracted into ethyl acetate. The product was purified via prep HPLC ($C_{18}$; gradient from 0.025 M $NH_4OAc$ to acetonitrile). The yield of the title compound (14) was 1.1 g (42%).

Example 2

Inhibition of ADP-Induced Platelet Aggregation

Isolation of Platelets: Human blood is obtained from informed healthy adult volunteers. Blood is collected into one-sixth volume of acid/citrate/dextrose (ACD) buffer (85 mM sodium citrate, 65 mM citric acid, and 110 mM glucose). Collected blood is placed in a water bath at 37° C. for 30 minutes. Blood is then centrifuged at 275×g for 16 minutes at room temperature and the platelet-rich plasma is removed and centrifuged at 2200×g for 13 minutes at room temperature. The platelet pellet is resuspended in 40 mL of HEPES-buffered Tyrode's solution (137 mM NaCl, 2.7 mM KCl, 1 mM $MgCl_2$, 2 mM $CaCl_2$, 12 mM $NaHCO_3$, 0.36 mM $NaH_2PO_4$, 5.5 mM glucose, 5 mM HEPES pH 7.4, 0.35% bovine serum albumin or 0.35% human serum albumin) containing 10 U/mL heparin and 5 µM (final concentration) prostaglandin $I_2$ ($PGI_2$). The platelet suspension is incubated in a 37° C. water bath for 10 minutes and then 5 µM (final conc.) $PGI_2$ is added just before centrifugation at 1900×g for 8 minutes. The resulting pellet is resuspended in 40 mL of HEPES-buffered Tyrode's solution containing 5 µM (final concentration) $PGI_2$ and then is incubated for 10 minutes in a 37° C. water bath. A small aliquot (500 µL) of the platelet suspension is removed for platelet counting. Prior to centrifugation 5 µM (final concentration) $PGI_2$ is added to the suspension and then the suspension is centrifuged at 1900×g for 8 minutes. The pellet is resuspended at a density of $5 \times 10^8$ cells/mL in HEPES-buffered Tyrode's solution containing 0.05 U/mL apyrase. Aggregation Studies: ADP-induced platelet aggregation is determined by measuring the transmission of light through a 0.5 ml suspension of stirred (1000 rpm) washed platelets in a lumi-aggregometer at 37° C. (Chrono-Log Corp. Havertown, Pa.). The baseline of the instrument is set using 0.5 ml of Hepes-buffered Tyrode's solution. Prior to aggregation measurements, the platelet suspension is supplemented with 1 mg/ml fibrinogen. Platelet aggregation is initiated by the addition of indicated concentrations of ADP or other agonists, and the light transmission is continuously recorded for at least 8 min. When inhibitors of platelet aggregation are tested, platelets are incubated for 2 min in the presence of indicated concentrations of inhibitor before addition of ADP or other agonists, and the response is recorded for at least 8 min. The potency of agonists and inhibitors of platelet aggregation is calculated from both the rate of aggregation and the maximal extent of aggregation obtained for each determination by fitting the data to a four-parameter logistic equation using the GraphPad software package (GraphPad Corp. San Diego, Calif.).

When a broad range of concentrations of $P2Y_{12}$ antagonist is tested (usually from 1 nM to 100 µM), an $IC_{50}$ value is also obtained. $IC_{50}$ values represent the concentration of antagonist necessary to inhibit by 50% the aggregation elicited by a given concentration of ADP.

Example 3

Inhibition of ADP-Induced Platelet Aggregation in Whole Blood

Human blood is obtained from informed healthy adult volunteers. Blood is collected into syringes containing heparin, sodium citrate, PPACK or hirudin as anticoagulant. Blood is carefully transferred to a conical tube and maintained at room temperature. Assays are conducted within 60 min from the collection of the blood sample. ADP-induced platelet aggregation is performed using the impedance mode of an aggregometer (Chrono-Log Corp. Havertown, Pa.). Blood is gently mixed and an aliquot of 500 µL is transferred to a measurement cuvette, then, 450 µL of warm sterile saline is added to each cuvette and the sample is stirred at 1000 rpm. The impedance probe is introduced into the cuvette and the sample is allowed to warm for approx. 3-4 minutes in the aggregometer. The basal impedance is recorded for 1 minute and then 50 µL of the appropriate concentrations of ADP are added to generate an ADP dose response curve. For the evaluation of $P2Y_{12}$ receptor antagonists on platelet aggregation, after the basal impedance is recorded for 1 minute as indicated above, blood samples are supplemented with 50 µL of the antagonist or vehicle and after 2 minutes, 50 µL of ADP ($EC_{90}$; usually 5-10 µmol/L ADP) are added and the impedance is recorded for up to 8 minutes. The potency of agonists and inhibitors of platelet aggregation is calculated from the impedance values obtained in each sample by fitting the data to a four-parameter logistic equation using the GraphPad software package (GraphPad Corp. San Diego, Calif.).

Example 4

$IC_{50}$ Values for Representative Compounds of the Present Invention

Platelet $IC_{50}$ data or % inhibition at a fixed concentration of putative antagonist (0.3 µM) were determined using washed human platelets, according to the protocol of Example 2. The agonist challenge (ADP) was typically in the range of 1-5 µM. The outcome of these experiments is presented in Table 1. Data are presented in µM and are from the average of two experiments or more.

TABLE 1

| Compound # | PLATELET DATA IC50 (uM) Washed Platelets |
|---|---|
| 1 | 0.319 |
| 2 | 0.279 |
| 3 | 0.404 |
| 4 | 0.105 |
| 5 | 0.536 |
| 6 | 0.297 |
| 7 | 0.385 |
| 8 | 0.134 |
| 9 | 0.744 |
| 11 | 0.57 |
| 12 | 0.2 |

TABLE 1-continued

| Compound # | PLATELET DATA IC50 (uM) Washed Platelets |
|---|---|
| 13 | 0.089 |
| 14 | 0.096 |
| 15 | 0.19 |
| 19 | 0.062 |
| 20 | 0.092 |
| 21 | 0.087 |
| 22 | 0.099 |
| 23 | 0.099 |
| 25 | 46% inh. @ 0.3 µM |
| 28 | 64% inh. @ 0.3 µM |
| 30 | 56% inh. @ 0.3 µM |
| 33 | 56% inh. @ 0.3 µM |
| 34 | 52% inh. @ 0.3 µM |
| 35 | 61% inh. @ 0.3 µM |

The data in Table 1 illustrates that a diverse set of compounds of the present invention show activity as antagonists of $P2Y_{12}$-mediated platelet aggregation. For example, compounds differing by either a cinnamyl acetal moiety (1-9) or a p-fluorophenyl acetal moiety (11-14, 19-22, 24, 28, 30, 33, and 34) and having various urea modifications in the base portion and various phenyl ether modifications at the 5' position of the ribose showed a range of potencies below 1 µM. In particular, substituents on the aromatic ring of the phenyl ether residue had a large influence on the potency. For compounds containing a p-fluorophenyl acetal moiety, having a methoxy group in the 3 position (19), a methoxy group in the 4 position (14, 20-23), or a fluorine in the 5 position (13) resulted in potencies of less than 0.1 µM. Taken together, Table 1 illustrates that a wide variety of molecules falling under the definition of Formula III can be useful as antagonists of $P2Y_{12}$ mediated platelet aggregation.

Example 5

In Vivo PK/PD Measurements Following Oral Administration

These compounds were administered intravenously and orally to compare the extent of absorption by the oral route to the intravenous route and evaluate their ability to inhibit platelet aggregation in vivo. The following brief protocol describes the experiment methodology.

While anesthetized by an inhaled anesthetic, male Sprague-Dawley rats were surgically cannulated in the jugular vein for blood sample collection in order to assess systemic exposure of the compound after oral or intravenous administration and platelet aggregation. For the oral studies, compounds were administered as suspensions of the free acid or sodium salt forms, or as solutions of the sodium salt forms. Animals were allowed 48 hours to recover prior to dose administration.

A blood samples was taken immediately prior to compound administration. This sample was used to assess the baseline platelet aggregation and potential drug interference in the LC/MS/MS analysis. Compound was administered by either oral gavage or tail vein and blood samples were withdrawn for plasma analysis at up to 12 time points ranging from 5 min to 24 hours following compound administration. LC/MS/MS was used to measure the amount of compound in the plasma after both routes of administration and the plasma exposure was compared between the oral and IV routes (%F). %F is the % of the administered dose that is absorbed after oral administration. This is calculated from the ratio of drug levels seen after the oral administration to that seen in the plasma following IV administration ("100% bioavailable"). If the AUC (area under the plasma concentration time curve) for both routes were the same then the oral route was considered 100% bioavailable. The in vivo platelet aggregation data that was acquired at similar time points was then compared to the plasma concentration and a calculation of the concentration needed to inhibit platelet aggregation was made.

Example 6

Oral Bioavailability (%F) for Representative Compounds of the Present Invention

The bioavailability of certain compounds of the present invention was determined following oral administration in rats, according to the protocol of Example 5. The compounds were administered as either a suspension of the free acid forms, a suspension of the sodium salt forms, or as a solution of the sodium salt forms. The result of these experiments is presented in Table 2.

TABLE 2

| Compound | % F | | |
| --- | --- | --- | --- |
| | free acid suspension | salt suspension | salt solution |
| 1 | 8.7-13.1 | — | 38.7-39.6 |
| 14 | — | 21.5-22.1 | 43.3-44.6 |
| 15 | 14.3-14.6 | 29.5-29.9 | 52.5-53.4 |

The data in Table 2 shows that Compounds 1, 14, and 15 had high bioavailability following oral administration.

As the table illustrates, bioavailability can be enhanced by administration of the compounds in their salt forms, which are more soluble under the aqueous conditions typically found in the gastrointestinal system. For example, compound 1 shows between 8 and 13% bioavailabilty when administered as a suspension of the free acid form, which increases to about 39% when administered as a solution of the sodium salt. A similar trend is seen for compounds 14 and 15, which show comparable bioavailabilities following solution administration of their sodium salt forms (ca. 44% and 53%, respectively).

Taken together, the data presented in Tables 1 and 2 demonstrates that compounds of the present invention show high antagonist potency towards the platelet $P2Y_{12}$ receptor, and can be highly bioavailable following oral administration. Consequently, they are potentially useful as therapeutics in diseases where inhibition of platelet aggregation would be beneficial, particularly in those applications where oral administration of said compounds is desirable.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed is:

1. A compound of Formula IIIa, or a tautomer thereof, or a salt thereof:

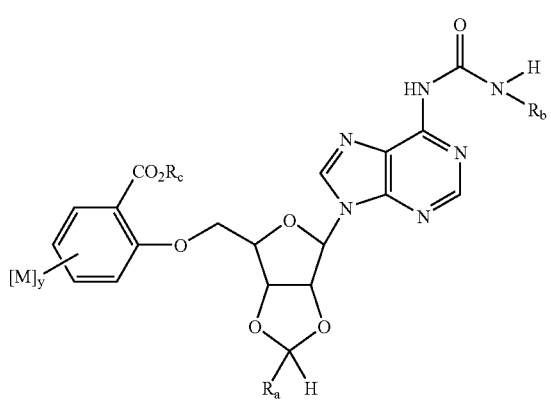

Formula IIIa wherein:
$R_b$=$C_{1-8}$ alkyl, $C_{3-7}$cycloalkyl, or $C_{4-11}$alkylcycloalkyl, with 1-2 carbons in the alkyl portion and 3-6 carbons in the cycloalkyl portion;
$R_a$=styryl;
$R_c$ is H, a physiologically-relevant cation forming a carboxylate salt, or alkyl;
M=hydrogen, halogen, $C_{1-4}$ alkyl, or $C_{1-4}$ alkoxy; and
y=1.

2. The compound according to claim 1, wherein said compound is Compound 1

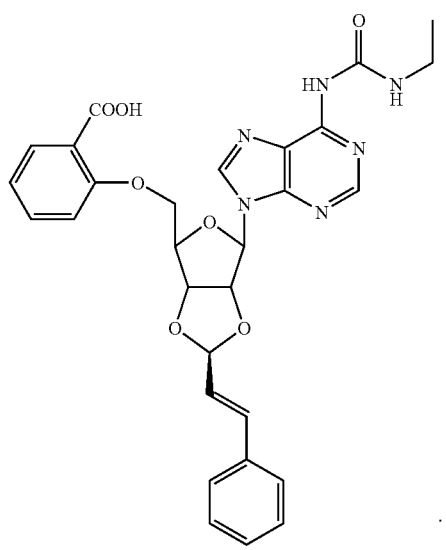

3. A compound of Formula IIIb, or a tautomer thereof, or a salt thereof:

Formula IIIb

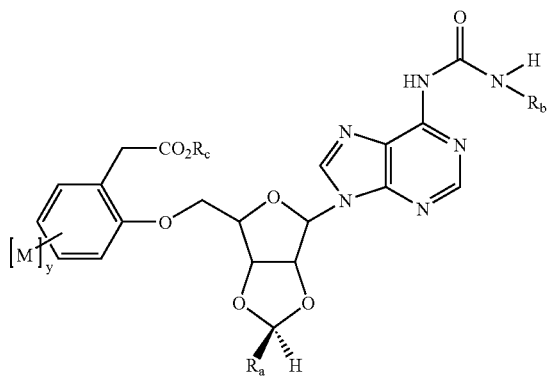

wherein:
$R_b = C_{1-5}$ alkyl, $C_{3-6}$ cycloalkyl, or $C_{3-6}$ alkylcycloalkyl, with 1-2 carbons in the alkyl portion and 3-6 carbons in the cycloalkyl portion;
$R_a$=trans p-fluorophenyl, or trans-styryl;
$R_c$ is H, a physiologically-relevant cation forming a carboxylate salt, or alkyl;
M=hydrogen, halogen, $C_{1-4}$ alkyl, or $C_{1-4}$ alkoxy; and
y=1 or 2.

4. The compound according to claim 3, wherein $R_a$=trans p-fluorophenyl.

5. The compound according to claim 3, wherein $R_a$=styryl.

6. The compound according to claim 5, wherein said compound is Compound 6

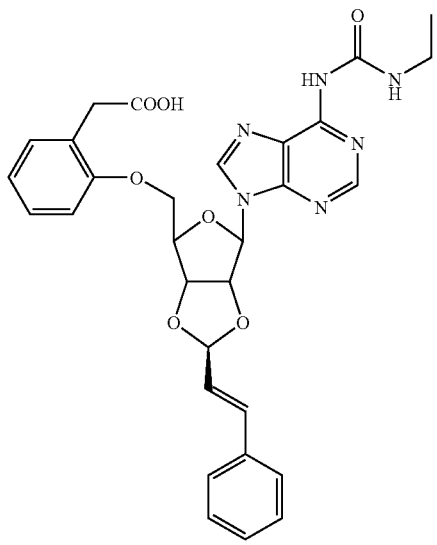

6

7. A compound of Formula IIIa, or a tautomer thereof, or a salt thereof:

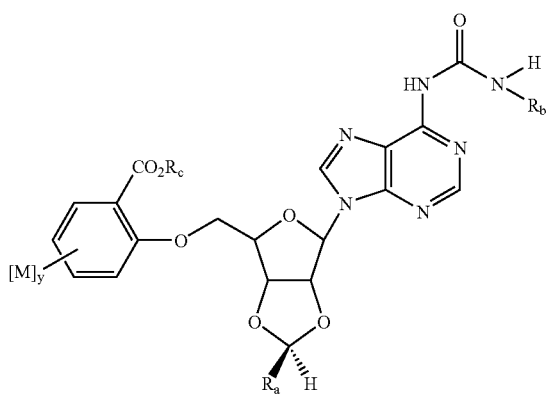

Formula IIIa wherein:
$R_b = C_{1-4}$ alkyl, $C_{3-6}$ cycloalkyl;
$R_a$=trans-phenyl, cis-phenyl, cis-benzyl, or trans-styryl;
wherein at least one of the hydrogens on each phenyl ring is substituted with a fluorine;
$R_c$ is H;
M=halogen, $C_{1-4}$ alkyl, or $C_{1-4}$ alkoxy; and
y=0-2.

8. The compound according to claim 7, wherein $R_a$=trans-styryl.

9. The compound according to claim 7, wherein $R_a$=trans-phenyl.

10. A method of treating diseases or conditions associated with increased platelet aggregation, comprising administering to a subject in need thereof a therapeutically effective amount of the compound according to claim 1 or 3, or a tautomer thereof, or a salt thereof, wherein said amount is effective to inhibit platelet aggregation.

11. The method according to claim 10, wherein said compound or the tautomer thereof, or the salt thereof, reversibly inhibits ADP-induced platelet aggregation.

12. The method according to claim 10, wherein said compound or the tautomer thereof, or the salt thereof, is administered in combination with other antiplatelet and/or anticoagulant drugs.

13. The method according to claim 10, wherein said diseases associated with increased platelet aggregation are disorders characterized by thrombosis, primary arterial thrombotic complications of atherosclerotic disease, thrombosis secondary to vascular damage and inflammation, indications with a diffuse thrombotic/platelet consumption component, venous thrombosis, coronary arterial thrombosis, pathological effects of atherosclerosis and arteriosclerosis, chronic or acute states of hyper-aggregability, reocclusion of an artery or vein following fibrinolytic therapy.

14. The method according to claim 13, wherein said thrombosis are unstable angina, or myocardial infarction; said primary arterial thrombotic complications of atherosclerosis are thrombotic stroke, peripheral vascular disease, or myocardial infarction said thromboses secondary to vascular damage and inflammation are vasculitis, arteritis, glomerulonephritis or organ graft rejection; said indications with a diffuse thrombotic/platelet consumption component are disseminated intravascular coagulation, thrombotic thrombocytopenic purpura, hemolytic uremic syndrome, heparin-induced thrombocytopenia, preeclampsia or eclampsia; said venous thrombosis are deep vein thrombosis, veno-occlusive disease, or hematological conditions; and said coronary arterial thrombosis is associated with unstable angina, coronary angioplasty or acute myocardial infarction.

15. The method according to claim 13, wherein said pathological effects of atherosclerosis and arteriosclerosis are arteriosclerosis, acute myocardial infarction, chronic stable angina, unstable angina, transient ischemic attacks, strokes, peripheral vascular disease, arterial thrombosis, preeclampsia, embolism, restenosis or abrupt closure following angioplasty, carotid endarterectomy, or anastomosis of vascular grafts; said chronic or acute states of hyper-aggregability is caused by DIC, septicemia, surgical or infectious shock, post-operative trauma, post-partum trauma, thrombotic thrombocytopenic purpura, snake venom or immune diseases.

16. The method according to claim 10, wherein said conditions associated with increased platelet aggregation and/or platelet activation are produced by the contact of blood with an artificial device.

17. The method according to claim 16, wherein said artificial device is a hemodialysis instrument, a paracorporeal artificial lung and an extracorporeal membrane oxygenation device, an internal implantable artificial heart, an apheresis instrument used to remove or isolate a specific component of the blood and returning the remaining blood components to a donor.

18. The method according to claim 10, wherein said systemic administration is oral administration.

* * * * *